United States Patent [19]

Staffieri

[11] 4,371,990
[45] Feb. 8, 1983

[54] THIGH PROSTHESIS

[76] Inventor: Lamberto Staffieri, 38069-Torbole sul Garda (Trento), Via Matteotti, 28, Italy

[21] Appl. No.: 159,710

[22] Filed: Jun. 16, 1980

Related U.S. Application Data

[63] Continuation-in-part of Ser. No. 112,763, Jan. 17, 1980, Pat. No. 4,268,923.

[30] Foreign Application Priority Data

Jan. 18, 1979 [IT] Italy .............................. 82201 A/79

[51] Int. Cl.³ ........................... A61F 1/04; A61F 1/08
[52] U.S. Cl. ................................................ 3/28; 3/29
[58] Field of Search ....................................... 3/22–29, 3/2

[56] References Cited

U.S. PATENT DOCUMENTS

| | | | |
|---|---|---|---|
| 2,542,567 | 2/1951 | Peters | 3/29 X |
| 3,806,958 | 4/1974 | Gusev | 3/22 |
| 3,820,169 | 6/1974 | Long et al. | 3/22 |
| 3,823,424 | 7/1974 | May | 3/22 |
| 3,901,223 | 8/1975 | May | 3/22 X |
| 4,145,766 | 3/1979 | May | 3/22 X |
| 4,215,442 | 8/1980 | Blatchford et al. | 3/22 |
| 4,268,923 | 5/1981 | Staffieri | 3/22 |

FOREIGN PATENT DOCUMENTS

| | | | |
|---|---|---|---|
| 599440 | 10/1925 | France | 3/22 |
| 175193 | 2/1922 | United Kingdom | 3/27 |

Primary Examiner—Ronald L. Frinks
Attorney, Agent, or Firm—Guido Modiano; Albert Josif

[57] ABSTRACT

A thigh prosthesis or artificial leg comprising an upper socket portion designed to be secured, in use, to an amputee's stump, a lower shin portion, an articulation frame joining the socket portion to the shin portion, resilient means for limiting and cushioning the articulation motion of the said articulation frame, and friction control means designed to control the relative articulation movements between the socket portion and the shin portion.

10 Claims, 7 Drawing Figures

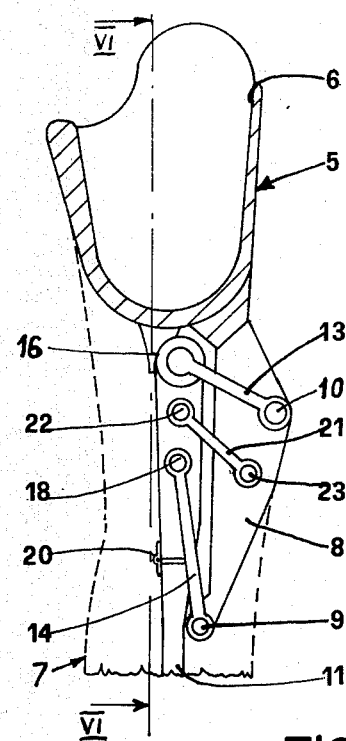

THIGH PROSTHESIS

CROSS-REFERENCE TO RELATED APPLICATIONS

This application is a continuation-in-part of the applicant's copending application, Ser. No. 6/112,763 filed on Jan. 17, 1980, now U.S. Pat. No. 4,268,923.

BACKGROUND OF THE INVENTION

The present invention relates to a thigh prosthesis or artificial leg designed to permit instinctive movements that amputees to whom a thigh has been amputated should effect to be able to keep in balance on the artificial leg and to walk.

An amputee to whom a thigh has been amputated is generally given an artificial leg or thigh prosthesis designed to be of the same length as his non-amputated leg. Such a prosthesis is often unsatisfactory as it is suitable to ensure only static balance. To obtain safe dynamic balance a thigh prosthesis sensitive to motion variations would be required.

Thigh prosthesis of the prior art are found to be quite cumbersome to use and difficult and expensive to manufacture. Some conventional artificial legs are also provided with braking devices to prevent the user from falling. However, braking devices are generally useless as they exert positive action only when the user has already lost his balance.

Furthermore, prior art artificial legs are designed to shorten during advance movement of the user's non-amputated leg (active deambulation phase), which results in the amputee's center of gravity being considerably lowered. Thus, in the following deambulation passive phase (i.e. when the artificial leg is lifted by the user to allow it to lengthen) the user must effect a considerable additional effort to raise his own center of gravity.

The most relevant prior art known to the applicant is: U.S. Pat. Nos. 3,901,223 and 4,145,766.

SUMMARY OF THE INVENTION

An object of this invention is to provide a thigh prosthesis or artificial leg adapted to provide static and dynamic balance while giving the amputee the possibility of taking advantage of his instinctive sense of balance.

Another object of the invention is to provide an artificial leg designed to prevent the user's center of gravity from lowering to any substantial extent during deambulation.

Another object of the invention is to provide a thigh prosthesis adapted to simulate natural gait.

Another object of the invention is provision of an artificial leg simple to produce and use which may be manufactured at low cost.

These and other objects are attained by a thigh prosthesis or artificial leg having a socket portion designed to receive and be secured, in use, to an amputee's stump, a shin portion, an articulation frame joining the socket portion to the shin portion, and resilient means for limiting and cushioning articulation movements of the said articulation frame, the improvement wherein the articulation frame is adapted sequentially to lengthen the prosthesis during an active deambulation phase and to shorten it during a passive deambulation phase and comprising yieldingly resisting means arranged to control extension and shortening movements of the said articulation frame.

BRIEF DESCRIPTION OF THE DRAWINGS

Further objects and advantageous features of the present invention will become more apparent from the following detailed description of the accompanying drawings, in which:

FIG. 3 is a diagrammatic view of an embodiment of a prosthesis similar to that if FIG. 1, in a standing position;

FIG. 4 shows the prosthesis of FIG. 3 in an extended position;

FIG. 5 is a cross-sectional view taken along the line V—V of FIG. 6 and shows another embodiment of a prosthesis in accordance with the invention;

FIG. 6 is a sectional view along line VI—VI of FIG. 5; and

DETAILED DESCRIPTION OF THE PREFERRED EMBODIMENTS

Figure 1:
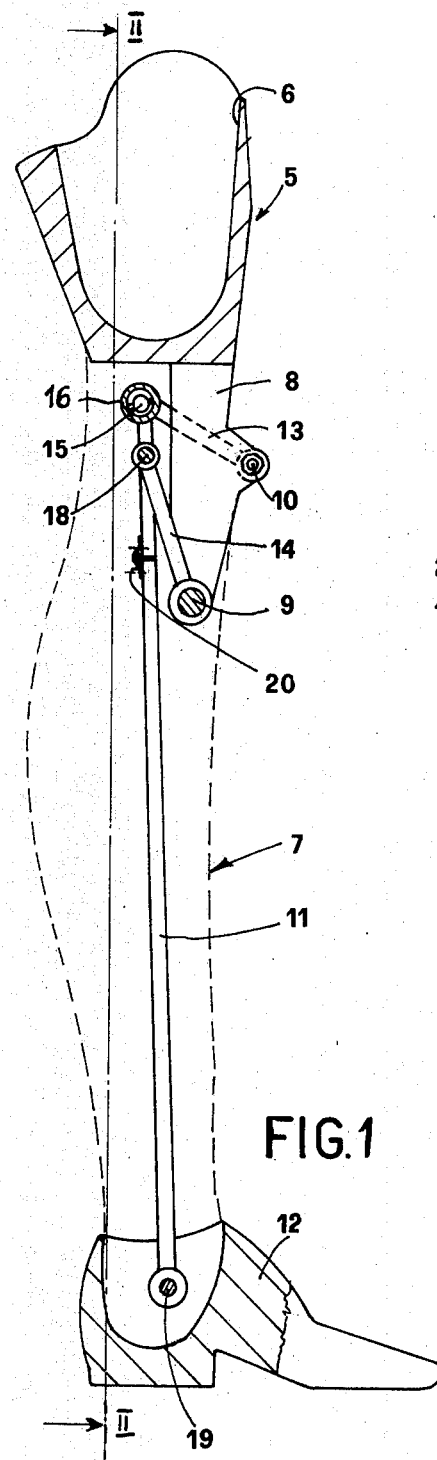
FIG. 1 is a cross-sectional view taken along the line I—I of FIG. 2.
Figure 2:
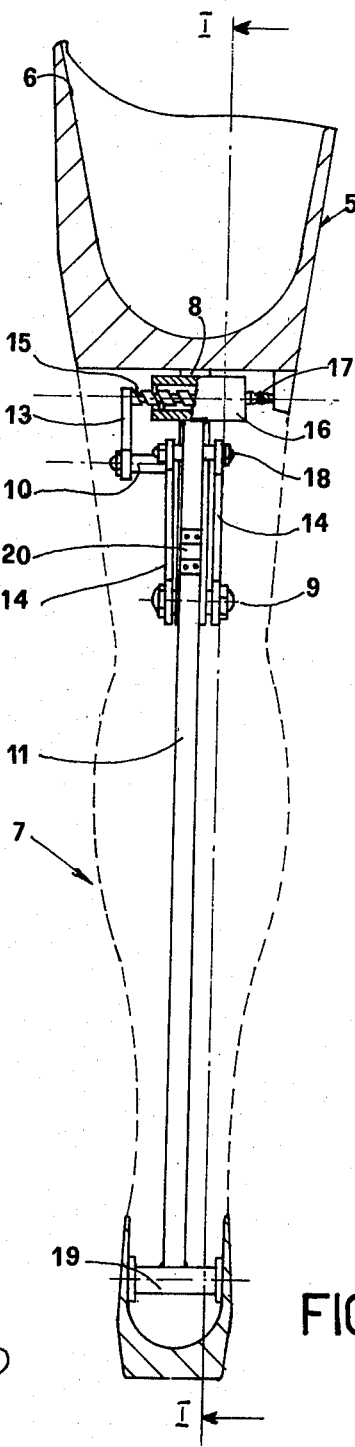
FIG. 2 is a cross-sectional view taken along line II—II of FIG. 1.

In the drawings like elements are indicated by the same reference numerals.

With reference first to FIGS. 1, 2 and 3, 4, the reference numeral 5 indicates an upper socket portion of a prosthesis or artificial leg whereas its lower shin portion is indicated by 7. The socket portion 5 delimits inside thereof a recess 6 designed to receive, and to be secured to, an amputee's stump. The socket portion 5 also has a downwardly extending rigid extension 8 arranged to carry a lower pivot 9 and an upper pivot 10. The pivot 10 is disposed slightly forwards with respect to the pivot 9 in the walking direction.

The shin portion comprises a rod 11 and a weight 12, preferably shaped as a foot. The shin portion 7 is articulated to the socket portion 5 by means of an upper link or a pair of upper links 13 and a lower link or a pair of lower links 14. The rod or pair of rods 13 has one end articulated to the upper end or top of the rod 11 by means of a pivot mounting 15, and its other end pivoted to the pin 10. As is better shown in FIG. 2, the pivot mounting 15 comprises a quick-thread screw screwable in a sleeve 16 which is fixed, e.g. by welding, to the top end of the rod 11. The screw 15 has one end secured to the link 13 and its other end preferably abuts against a resilient cushioning means 17 such as a piece of rubber or a compression spring or the like. The pin 10 laterally projects from the extension 8 so that the link 13 can rotate about, and slide along, it to be able to follow screwing and unscrewing movements of the pin 15.

It will be seen that the link 13 extends transversely with respect to a vertical axis x—x (FIG. 3).

The lower rod or pair of rods 14 has one end pivoted to the pin 9 and its other end articulated to the rod 11 by means of a pin 18 which is arranged at a level higher than that of the pin 9.

It should be noted that the extension 8, the links 13 and 14 and the rod 11 are the components of an articulation parallelogram frame arranged to permit the rod 11 to be displaced (when the upper portion 5 is moved forwards in the direction of the arrow A in FIG. 3) from a standing position (shown in FIGS. 1 and 3) to an extended position (shown in FIG. 4). When the artificial leg is in a standing position, the rod 11 is arranged slightly inclined with respect to a vertical axis. When the artificial leg is being moved to an extended position, the weight or foot 12 is moved away from, or left behind with respect to, the socket portion 5. Thus, while the user of the prosthesis effects a passive deambulation phase (i.e. when the artificial leg is lifted by the user to permit its shortening), the weight 12 is moved forwards, mainly, owing to gravity, to the standing position shown in FIGS. 1 and 3.

The length of each step effected by the artificial leg is determined by resilient abutments, limit means or the like, not shown, e.g. located on the extension 8. Limit means is also provided inside the foot 12 (FIGS. 1 and 2) to cushion its connection to the rod 11 by means of a pin 19. The pin 19 is preferably supported by rubber bearing blocks to further assist in cushioning the movements of the prosthesis.

The rod 11 preferably comprises two lengths articulated to one another by means of a hinge 20 to allow the user to bend the artificial leg, e.g. while sitting on a chair.

FIGS. 5 and 6 show an embodiment of the prosthesis in accordance with the invention, in which an additional intermediate link or pair of links 21 is provided. The link 21 has one end articulated to the rod 11 by means of a pin 22 and its other end is pivoted to the extension 8 by way of a pin 23. The link 21 is an auxiliary link arranged substantially parallel to the link 13, thereby obtaining an articulation frame having six articulation pins to ensure better distribution of stresses both along the rod 11 and the extension 8.

Figure 7:
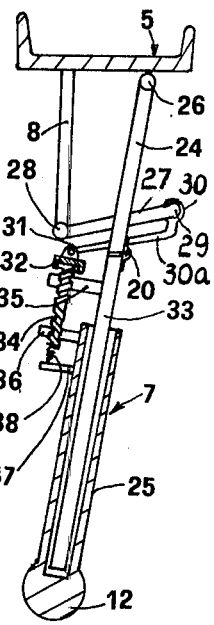
FIG. 7 is a cross-sectional view of another embodiment of a prosthesis in accordance with the invention.

FIG. 7 shows a further embodiment of the prosthesis in accordance with the invention, in which the shin portion 7 comprises a rod 24 telescopically connected to a tubular member 25. The rod 24 is pivoted, by means of a pin 26, to the upper portion 5, whereas the tubular member 25 terminates at its lower end with the weight 12. Both the rod 24 and the tubular member 25 can have a circular, rectangular or the like configuration in cross-section to prevent rotation with respect to one another. The tubular member 25 is articulated to the extension 8 by means of an articulation frame comprising a first link 27 having one end pivoted at 28 to the extension 8 and its other end pivoted at 29 in an assembly comprising a spring-loaded pin 29 received in a sleeve 30. The sleeve 30 is rigid with a second link 30a which is pivoted at 31 to a transmission member 32. The pins 28, 29 and 31 are all arranged in a sustantially horizontal direction and parallel to each other.

The transmission member 32 has a recess designed to receive therein a quick-thread screw 34 one half of which is right handed and the other half left handed. The screw 34 is held by the transmission member 32 so as to be able to rotate therein. The screw engages at one end thereof with a projecting element 35 rigid with the rod 24, whereas its other and is screwed in a projecting element 36 rigid with the tubular member 25. Close to the tubular member 25 a leg 37 is provided against which one end of a spring 38 abuts, the other end of the spring engaging with the screw 34. Thus, telescopic movements of the rod 24 in and out the tubular member 25 are controlled by the screw 34 to ensure safe, confortable and smooth deambulation.

It will be understood that both the pin 15—sleeve 16 connection in the articulation frame of the embodiments shown in the FIGS. 1 to 6 and the screw 34—projecting elements 35, 36 arrangement in the embodiment of FIG. 7 act among other things, as yieldable control means for the relative articulation movements between socket portion 5 and shin portion 7 to ensure progressive and smooth extension and shortening movements of the articulation frame. The articulation frame may also comprise some equivalent friction coupling in addition to, or in lieu of, the above-described control means.

With a thigh prosthesis or artificial leg in accordance with the present invention it is thus possible for the user to keep, during deambulation, his center of gravity substantially at a constant level from the ground, and to take advantage to a maximum extent of his instinctive sense of balance.

I claim:

1. In a thigh prosthesis or artificial leg having a socket portion designed to receive and be secured, in use, to an amputee's stump, a shin portion, and an articulation frame joining the socket portion to the shin portion, and resilient means for limiting and cushioning articulation movements of the said articulation frame, the improvement wherein the articulation frame is adapted sequentially to lengthen the prosthesis during an active deambulation phase and to shorten it during a passive deambulation phase and comprises yieldingly resisting means arranged to control extension and shortening movements of the said articulation frame.

2. A thigh prosthesis as set forth in claim 1, wherein the said yieldingly resisting means comprises a friction coupling.

3. A thigh prosthesis as set forth in claim 2, wherein the friction coupling comprises a quick-thread screw articulation.

4. A thigh prosthesis as set forth in claim 3, wherein the quick-thread screw articulation comprises a sleeve rigid with the shin portion and a quick-thread pin in screw engagement with the said sleeve, the said pin having one end thereof secured to a link of the said articulation frame and its other end in abuting engagement with resilient cushioning means.

5. A thigh prosthesis as set forth in claim 1, wherein the said articulation frame comprises an articulated parallelogram arrangement.

6. A thigh prosthesis as set forth in claim 1, wherein the said articulation frame comprises six articulation pins.

7. A thigh prosthesis as set forth in claim 1, wherein the said shin portion comprises a rod and a balancing weight adapted to act as a foot.

8. A thigh prosthesis as set forth in claim 7, wherein the said shin portion is telescopically connected to the said weight.

9. A thigh prosthesis as set forth in claim 8, wherein the articulation frame comprises a quick-thread screw having a right-handed threaded portion in engagement with the said rod and a left-handed threaded portion in engagement with the said weight, a control head adapted to rotatably receive the said screw, a spring-loaded pin seated in a sleeve, a first link having one end thereof articulated to the said control head and its other end secured to a sleeve, a second link having one end thereof articulated to the said socket portion and a third link having one end thereof secured to the said spring-loaded pin and its other end secured to the other end of the said secured link.

10. A thigh prosthesis as set forth in claim 1, wherein the shin portion comprises two lengths connected to one another by a hinge.

* * * * *